United States Patent [19]

Skrabanja et al.

[11] Patent Number: 5,929,028
[45] Date of Patent: Jul. 27, 1999

[54] LIQUID GONADOTROPIN CONTAINING FORMULATIONS

[75] Inventors: Arnold Titus Philip Skrabanja, An Nijmegen; Petrus Johannes Maria van den Oetelaar, Et Heesch, both of Netherlands

[73] Assignee: Akzo Nobel, N.V., Arnhem, Netherlands

[21] Appl. No.: 09/006,812

[22] Filed: Apr. 14, 1998

[30] Foreign Application Priority Data

Jan. 15, 1997 [NL] Netherlands ............. 97200099

[51] Int. Cl.$^6$ ............. A01N 37/18; A61K 38/16
[52] U.S. Cl. ............. 514/2; 514/8; 514/12; 514/800; 530/398; 530/399; 424/452; 424/418; 424/455
[58] Field of Search ............. 530/398, 399; 514/12, 8, 2; 424/452, 418, 455

[56] References Cited

U.S. PATENT DOCUMENTS

| | | | |
|---|---|---|---|
| 4,357,934 | 11/1982 | Fahim et al. | 128/1 R |
| 4,457,916 | 7/1984 | Hayashi et al. | 424/101 |
| 5,114,948 | 5/1992 | Conine et al. | 514/288 |
| 5,272,135 | 12/1993 | Takruri et al. | 514/12 |
| 5,338,835 | 8/1994 | Boime et al. | 530/398 |
| 5,384,132 | 1/1995 | De Meere et al. | 424/499 |
| 5,650,390 | 7/1997 | Samaritani et al. | 514/8 |
| 5,730,969 | 3/1998 | Hora et al. | 424/85.1 |
| 5,767,067 | 6/1998 | Arpaia et al. | 514/8 |

FOREIGN PATENT DOCUMENTS

| | | |
|---|---|---|
| 4481846 | 9/1993 | European Pat. Off. . |
| WO 96/29095 | 9/1996 | Netherlands ............. 47/26 |
| W) 9311788 | 6/1993 | WIPO . |
| WO 9322335 | 11/1993 | WIPO . |
| WO 96/29095 | 9/1996 | WIPO . |
| WO 9629095 | 9/1996 | WIPO . |

OTHER PUBLICATIONS

Schroeder, W.; "Methods for Partial Hydrolysis of the Polypeptide Chain" in The Primary Structure of Proteins, Harper & Row:NewYork, 1968, Chapter 9.

*Primary Examiner*—Cecilia J. Tsang
*Assistant Examiner*—Fabian A. Jameison
*Attorney, Agent, or Firm*—Mary E. Gormley

[57] ABSTRACT

The invention concerns a liquid gonadotropin-containing formulation characterised in that the formulation comprises a gonadotropin and stabilising amounts of a polycarboxylic acid or a salt thereof and of a thioether compound. The particular proteins (e.g. LH, TSH, FSH, or HCG) are in admixture with the particular stabilizers in an aqueous solution. The preparations contain a sufficient amount of the polycarboxylic acid or a salt thereof, preferably sodium citrate, and a sufficient amount of the thioether compound, preferably methionine, to stabilize the protein. The preparations preferably also include a nonreducing disaccharide like sucrose, and a non-ionic surfactant.

14 Claims, No Drawings

ND CONTAINING
LIQUID GONADOTROPIN CONTAINING FORMULATIONS

FIELD OF THE INVENTION

This invention relates to a liquid gonadotropin-containing formulation, to a method of preparation of said formulation, to a cartridge containing said formulation, and to a device for administration comprising said cartridge.

BACKGROUND OF THE INVENTION

The gonadotropins form a family of structurally related glycoprotein hormones. Typical members include chorionic gonadotropin (CG), follicle stimulating hormone (FSH; follitropin), luteinizing hormone (LH; lutropin) and thyroid stimulating hormone (TSH; thyrotropin). FSH, LH and TSH are present in most vertebrate species and are synthesized and secreted by the pituitary. CG has so far been found only in primates, including humans, and in horses and is synthesized by placental tissue. FSH and LH are the pituitary hormones essential for follicular maturation and luteinization in the female and for testis maturation and spermatogenesis in the male. Purified FSH administered alone or in combination with semipurified human menopausal gonadotropins containing a mixture of FSH and LH has been used, among others, to stimulate the development of ovarian follicles, as is required for assisted reproduction techniques, such as the IVF (in vitro fertilization) method. Human FSH, partially purified from urine is also used clinically to stimulate follicular maturation in anovulatory women with chronic anovulatory syndrome or luteal phase deficiency. In males a combination of FSH and LH have been used in a variety of conditions related to male infertility.

In recent years very pure preparations, of the gonadotropins have become available through the use of recombinant DNA technology (see for instance Boime et al., Seminars in Reproductive Endocrinology 10, 45–50, 1992: "Expression of recombinant human FSH, LH and CG in mammalian cells"). The recombinant gonadotropins are of constant quality i.e. have reproducible biochemical and biological properties. Genomic and cDNA clones have been prepared for all subunits and their primary structure has been resolved. Moreover, Chinese Hamster Ovary (CHO) cells have been transfected with human gonadotropin subunit genes and these cells are shown to be capable of secreting intact dimers (e.g. Keene et al (1989), J.Biol.Chem., 264, 4769–4775; Van Wezenbeek et al (1990), in From clone to Clinic (eds Crommelin D. J. A. and Schellekens H.), 245–251). It has been demonstrated that the biochemical and biological characteristics of e.g. recombinant FSH are almost identical to those of natural FSH (Mannaerts et al (1991), Endocrinology, 129, 2623–2630). Moreover, pregnancies were achieved after controlled ovarian superovulation using recombinant FSH (Germond et al (1992), Lancet, 339 ,1170; Devroey et al (1992), Lancet, 339, 1170–1171).

Structurally the gonadotropins are heterodimers composed of two dissimilar subunits, named α and β, which are associated by non-covalent bonds. Within a species, the α-subunit is essentially identical for each member of the gonadotropin family; it is also highly conserved from species to species. The β-subunits are different for each member, i.e. CG, FSH, TSH and LH, but show considerable homology in structure. Furthermore, also the β subunits are highly conserved from species to species. In humans, the α subunit consists of 92 amino acid residues, whilst the β subunit varies in size for each member: 111 residues in hFSH, 121 residues in hLH, 118 residues in hTSH and 145 residues in hCG (Combarnous, Y. (1992), Endocrine Reviews, 13, 670–691; Lustbader, J. W. et al. (1993), Endocrine Reviews, 14, 291–311). The β subunit of hCG is substantially larger than the other β subunits in that it contains approximately 34 additional amino acids at the C-terminus referred to herein as the carboxy terminal protein (CTP).

Relatively pure gonadotropin preparations are commercially available. For example, compositions containing naturally derived human menopausal gonadotropin (hMG), with FSH and LH activities in a ratio of approximately 1:1, and naturally derived human chorionic gonadotropin (hCG) are available, for example, as freeze-dried preparations under the trade names Humegon® and Pregnyl®, respectively, from N. V. Organon, Oss, The Netherlands. A freeze-dried recombinant human FSH (recFSH) preparation is, for example, available under the trade name Puregon® from the same company. The recombinant FSH is likewise in use for ovulation induction and for controlled ovarian hyperstimulation.

The stability of proteins in aqueous formulations is generally a problem in pharmaceutical industry. Likewise the stability of aqueous solutions of the gonadotropins is insufficient to allow storage for longer times. This is especially true for preparations containing the very pure gonadotropins, prepared using recombinant DNA methods, in relatively dilute solutions. Usually therefore those preparations are stored in a dry form, as is obtained after lyophilization. A stabilized gonadotropin containing lyophilized pharmaceutical formulation is disclosed in European Patent No. 448,146 (Akzo N. V.). These preparations contain organic carboxylic acids, particularly citric acid, and optionally a non-reducing sugar such as sucrose. Another solid gonadotropin containing pharmaceutical composition comprising sucrose as a stabilizer is disclosed in the International Patent Application WO 93/11788 (Applied Research Systems ARS Holding N. V.).

Although these freeze-dried preparations are stable enough to guarantee sufficient shelf-lifes, they have the disadvantage that prior to administration reconstitution is necessary. The patient therefore necessarily has to reconstitute the dried glycoprotein in a solvent before use, which is a disadvantage and an inconvenience to the patient. In addition, the solvent must be provided together with the freeze-dried preparation of the gonadotropin.

For a patient, who needs injections of a gonadotropin at regular times, for instance a patient receiving a daily dose of recFSH for ovulation induction, it would be of importance that the gonadotropin formulation is easy to handle, to dose and to inject. The reconstitution of a freeze-dried gonadotropin preparation demands prudence and carefulness and should be avoided if possible. It would facilitate the use of gonadotropins, if these glycoproteins could be produced and distributed as a stable solution to the patient, who could inject the medicament directly without reconstitution. In addition, a freeze-drying process is a costly and time consuming process step, and it would be an advantage if this step could be avoided when preparing a gonadotropin formulation.

A need exists therefore in a ready-for-use injection preparation, having a sufficient stability to guarantee a reasonable shelf-life.

In WO 93/22335 (COR Therapeutics Inc.) storage stable liquid compositions of substantially pure polypeptides are disclosed, which are prepared by dissolving the polypeptide in a citrate buffer of pH 5.0 to 5.5. Liquid formulations containing the gonadotropin recombinant-hCG stabilized with a non reducing sugar, preferably mannitol, in an aqueous solution in a phosphate buffer at pH 7, are disclosed in WO 96/29095 (Applied Research Systems ARS Holding N. V.).

Solutions comprising gonadotropins and a polycarboxylic acid salt are known from European Patent 448,146 (Akzo N. V.). These solutions, containing for instance citric acid, are described for preparing stabilized lyophilised gonadotropin formulations.

On storage of such solutions per se for longer times (months at room temperature) the gonadotropins are insufficiently stable.

SUMMARY OF THE INVENTION

The invention relates to a liquid gonadotropin-containing formulation which comprises a gonadotropin and stabilising amounts of a polycarboxylic acid or a salt thereof and of a thioether compound. The gonadotropin-containing formulations of the invention have improved stability on prolonged storage in comparison with formulations in which the thioether compound is lacking.

The term polycarboxylic acid, as used herein, means an organic acid having two or more carboxylic acid moieties. Typical polycarboxylic acids are citric acid, isocitric acid, tartaric acid, aspartic acid, glutamic acid or mixtures of these acids. Any pharmaceutically acceptable salt can be used, in particular salts of the alkali or alkaline earth metals, such as sodium, potassium, and calcium. A preferred salt is the sodium salt.

The term thioether compound means a compound which comprises an alkylthioalkyl function having the formula $R_1$—S—$R_2$—, wherein $R_1$ is lower alkyl, and $R_2$ is lower alkylene. The term lower alkyl means a branched or unbranched alkyl group having 1–6 carbon atom, such as hexyl, pentyl, butyl, tert-butyl, propyl, isopropyl, ethyl or methyl. The preferred lower alkyl group is methyl. The term lower alkylene means an alkylene group having 1–6 carbon atoms, such as 1,6-hexanediyl, 1,5-pentanediyl, 1,4-butanediyl, 1,3-propanediyl, propylidene, 1,2-ethanediyl, ethylidene or methylene. Preferably, the thioether compounds have an alkylthioalkyl function which corresponds to the side chain of an α-amino acid, such as in the amino acids methionine, homo- and nor-methionine, either as the D- or the L-enantiomer, or as the racemic mixture. The preferred thioether compound is the amino acid methionine ($R_1$ is methyl; $R_2$ is 1,2-ethanediyl).

DETAILED DESCRIPTION OF THE INVENTION

The liquid gonadotropin containing formulations of the invention comprise the gonadotropin in admixture with the particular stabilizers in solution. The formulation will contain a sufficient amount of a polycarboxylic acid, or a salt thereof, and of a thioether compound to stabilize the gonadotropin in solution for a desired time at a desired temperature.

The gonadotropin or gonadotropin derivatives, as used in the definition of the formulation of the present invention, are the proteins described above, e.g. follicle stimulating hormone (FSH), thyroid stimulating hormone (TSH), human chorionic gonadotropin (hCG), luteinizing hormone (LH), or derivatives, or analogs, and mixtures thereof, with or without other protein components.

The gonadotropin may be isolated from natural sources, e.g. from human urine, or the gonadotropin may be prepared in a (bio)synthetic way, c.f. by recombinant DNA techniques. Recombinant gonadotropins may for instance be prepared as described in Keene et al. (1989), "Expression of Biologically Active Human Follitropin in Chinese Hamster Ovary Cells", The Journal of Biological Chemistry, 26, 4769–4775, or as described by Reddy et al. in the International Patent Application WO 86/04589 (Applied Research Systems ARS Holding N. V.).

As used herein, a gonadotropin, for example follicle stimulating hormone (FSH), includes the compound's analogs, and its recombinant, natural, deglycosylated, unglycosylated, modified glycosylated, and other forms. As an example, the modified forms of gonadotropins, wherein the carboxy terminus of the protein is extended with a carboxy terminal peptide (CTP), the sequence of which is derived from the β subunit of human chorionic gonadotropin (the CTP sequence represents the amino acid residues 112–118 to 145 of the hCG β subunit, or a variant thereof), as described in European Patent 0,461,200 (Washington University), are included in the definition of gonadotropin. Examples of such modified forms are recombinant FSH-CTP and recombinant LH-CTP.

The most preferred gonadotropin is FSH produced by recombinant DNA techniques (recFSH), either alone or in admixture with LH or hCG. FSH purified from natural sources is generally only partially purified. The (protein) impurities seem to act to stabilize it somewhat. With recFSH, however the impurities are not present and thus the FSH, being present in comparatively low concentration on the basis of protein, is more susceptible to rapid degradation.

As used herein, "stabilize" is a relative term. To stabilize a liquid gonadotropin containing formulation with a stabilizing agent or compound means the ability to prevent or delay a decrease in the activity of the gonadotropin with the stabilizer. For example, a preparation would be deemed "stabilized" if, with the addition of a stabilizing compound ("stabilizer") it took longer (e.g. 2 weeks instead of 1 week) to degrade at a set temperature, thus loosing some of its in vivo and/or in vitro activity in comparison with the preparation without the stabilizer.

The gonadotropins activity may be determined by known methods relating to the particular gonadotropin. One possible measure of activity can be made by determining the amount of (inactive) oligomers, or modified (e.g. oxidized) monomers of the α- and β-subunits, formed over time. Oligomer formation in a sample can be determined by HPSEC (high performance size exclusion chromatography). Other methods of determining the residual activity of, for example recFSH, include enzyme immunoactivity assay (EIA) as described in U.S. Pat. No. Reissue 32,696 to Schuurs et al.; a kit available under the trade designation FSHEIA from BioMérieux of Marcy l'Etoile 69260 Charbonniéres-les-Bains, France for FSH; and in vitro bioassay of both FSH, FSH-CTP and LH as described in Mannaerts et al, Applications of in vitro Bioassays for Gonadotropins, Neuroendocrinology of Reproduction, pp. 49–58 (Elsevier Science Publishers BV, Amsterdam, NL 1987).

In a preferred embodiment of the invention the liquid gonadotropin containing formulation comprises as stabilizers a sufficient amount of a citric acid salt, preferably sodium citrate and a sufficient amount of the thioether compound methionine (racemic DL mixture).

When sodium citrate and methionine are the selected stabilizers in a liquid formulation according to the invention a suitable concentration of sodium citrate is 25–100 mM and a suitable concentration of methionine is 1–10 mM.

It has been found that the incorporation of a nonreducing disaccharide, such as sucrose or trehalose, into a formulation, which already comprises a polycarboxylic acid, or a salt thereof, and a thioether compound as stabilizers, further increases the stability of the gonadotropin in the liquid formulation. Sucrose is the preferred disaccharide in formulations according to the invention. A concentration of sucrose of approximately 25–300 mM is a suitable amount. Especially preferred are liquid gonadotropin-containing formulations comprising recombinant FSH or a derivative thereof, sodium citrate and methionine as the stabilizers and a further amount of sucrose. When recFSH of RECFSH-CTP is the gonadotropin to be stabilized in a liquid formulation a preferred amount of sucrose is 50 mg/mi.

The formulation of the invention preferably also comprises one or more nonionic surfactants. These surfactants act as anti-adsorption agents and prevent the loss of the gonadotropin as a result of adsorption of the protein to the walls of the container in which the formulations are kept. The addition of an anti-adsorption agent to the formulations of the invention is especially required when the formulations comprise a recombinant gonadotropin in low concentrations.

Preferred nonionic surfactants are Polysorbate 20, NF (Tween 20 available from Atlas Chemical Company), Polysorbate 80, NF (Tween 80 available from Atlas Chemical Company), Brij 35 (available from ICI Pharmaceuticals), and Pluronic F123 (available from BASF). Polysorbate 20, NF (Tween 20) is especially preferred.

Polysorbate is preferably understood as meaning a polysorbate which meets the specification of USP/NF XXII, which is published as "The National Formulary", p. 1763 and p. 1967, Official from 1 Jan. 1990 (22nd ed., US Pharmacopeial Convention, Inc. 1989).

An anti-adsorption agent or anti-adsorption agents will be present in such amounts that adsorption of the protein onto container walls, or walls of vessels, or glass ware used during processing, is decreased. Illustratively, amounts of Polysorbate 20 sufficient to form a concentration between about 0.1 and 0.2 mg/ml in the ultimate formulation for use are preferred.

The liquid formulation of the present invention has a pH between 6 and 8, and preferably between 6.5 and 7.2. Most preferred is a solution having a pH of about 7.0. At these pH ranges the liquid formulations of the invention are found to be the most stable.

The stable formulation of the instant invention can be prepared by admixing the selected gonadotropin in aqueous solution with sufficient amounts of a polycarboxylic acid or salt stabilizer and of a thioether compound stabilizer to stabilize the protein, after which optionally an amount of a nonreducing disaccharide and/or a nonionic sufactant are dissolved in the mixture. The pH of the resulting solution is then adjusted to a value between 6.5 and 7.2, and the solution is (sterile) filtered.

As used herein, an aqueous solution is a solution containing water, preferably water of suitable quality for parenteral administration (Water for Injection USP), as the primary, but not necessarily the only solvent. Small amounts of pharmaceutically admissible water miscible solvents like ethanol may be present as a cosolvent.

In a preferred embodiment of the present invention there is provided a method of preparation a liquid gonadotropin formulation comprising admixing, in an aqueous solution, at least one gonadotropin with an amount of sodium citrate to a concentration of 25–100 mM, and an amount of methionine to a concentration of 1–10 mM; optionally dissolving an amount of sucrose in said admixture to a concentration of 25–300 mM and optionally dissolving a nonionic surfactant, preferably Polysorbate 20, in said admixture; and adjusting the pH of the resulting solution to a value between 6.5 and 7.2, whereupon the solution may be sterile filtered. General methods for the preparation of parenteral formulations, especially concerning the measures to be taken for the formulations to be sterile, are known in the art, for instance as described in Gennaro et al., Remington's Pharmaceutical Sciences (18th Edition, Mack Publishing Company, 1990, see part 8 "Pharmaceutical Preparations and their Manufacture", and especially the chapter on "Parenteral Preparations" at pp 1545–1569).

Any gonadotropin used is preferably present in the formulations in a quantity sufficient to form a therapeutically useful concentration of the protein for parenteral (e.g. subcutaneous, intramuscular or intravenous) administration.

Useful doses of gonadotropins are known to medical practitioners, and the amount included in a dose is generally dependent upon the disease state and the particular patient being treated.

For example for FSH, useful doses range from about 25 to 1500 International Units (lU), especially 50–225. Approximately 75 lU is considered a therapeutic amount.

Illustratively, amounts as high as 10,000 international units and as low as 15 international units of HCG have been administered. Injections ranging from 20 to 225 international units LH have been used.

The concentration of gonadotropin in the liquid formulations of the invention is dependent on the solubility of the gonadotropin and on the therapeutic amount for a given dose.

The preferred liquid formulations of the present invention are the formulations that comprise as the gonadotropin the recombinant proteins recFSH or the recFSH-CTP derivative thereof. A suitable concentration of recFSH may range from about 20–2000 lU/ml, which roughly corresponds with a concentration of 2–200 µg/ml (for a preparation having a specific FSH activity of 10.000 lU/mg protein). A preferred range is from 500–1500 lU/ml.

In one preferred embodiment, a combination of FSH and LH or FSH and HCG are dissolved together to from a formulation having therapeutic amounts of both of the selected gonadotropins.

The liquid gonadotropin containing formulations of the invention may be stored in the liquid state at various temperatures for prolonged periods while retaining the biological activity and physical stability of the gonadotropin. Preferably the storage temperature is below 30° C. and above the freezing temperature. The preferred storage temperature range is between approximately 2° C. and 8° C.

The liquid gonadotropin containing formulations of the invention can be freeze-dried, if desired.

In a further aspect of the invention there is provided a cartridge containing a sterile liquid formulation according to the invention. As used herein a cartridge means a closed container, such as an ampoule, a vial, a bottle or a bag.

A cartridge may contain an amount of the liquid gonadotropin formulation corresponding to one or more therapeutic doses of the gonadotropin. In a further aspect of the invention there is provided a device for administration comprising a cartridge containing a sterile liquid formulation according to the invention. A preferred device for administration is a pen-type injector, which comprise means for easy adjustment of the amount of a formulation that is to be injected. Such pen type injectors are known per se, such as for instance the well known B-D Pen (a trademark of Becton Dickinson and Company), an insulin-injection system.

As implied above, the liquid gonadotropin formulation made availabe by the present invention solves a problem in that, quite contrary to the state of the art, a preparation is provided which can be injected directly, i.e. without the necessity for the patient to reconstitute a dried product before use. In this respect, the invention also pertains to the use of a gonadotropin for the manufacture of a directly injectable liquid medicament for the treatment of infertility.

As such preparations are neither in existence, nor obvious from the current, complicated injection preparations, said use was not expected in view of the prior art, and has evident advantages in the treatment of patients.

The directly injectable liquid medicament may be held in a container such as a vial or an ampoule, i.e. a container of the type from which it can be directly taken up and sucked into an injection device. It may also be contained in a cartridge of the type that as such can be placed in an injection device adapted for receiving such a cartridge, an example of which is the pen-injector of the type referred to above. It should be noted that it is an additional advantage of the invention, that the liquid medicament can be in the form of a cartridge for multiple use. Using an injector with a suitable scale indication, the patient can simply inject each time the quantity needed. The aforementioned B-D pen-injector, normally used for insulin, has a convenient system to adjust the quantity to be injected, and can relatively easily be provided with a scale indication adapted to the liquid gonadotropin-containing medicament.

In respect of the above, the invention also resides in a method of treating infertility by the administration of gonadotropin, wherein the administration is done by injecting liquid gonadotropin directly from an administration device, such as a pen type injector, loaded with a cartridge containing a stable, liquid formulation of gonadotropin.

The invention is further explained with reference to the following Examples.

EXAMPLE 1

Formulations containing recombinant FSH.

Liquid formulations containing recombinant FSH, having the compositions as depicted in Table I, and denoted A-J, were prepared. 0.5 ml aliquots of each composition were stored, in a closed 2 ml vial, for up to 2 months at 8° C., 30° C. and 40° C., respectively.

The in vitro bioactivity of the stored recFSH samples was than measured, by determining the extent of stimulation of a cell wherein a human FSH receptor is expressed. Activity is measured as the amount of cyclic AMP which is released upon binding of the FSH at the FSH receptor. In Table II the bioactivity of a the FSH-samples, stored for the indicated time and at the indicated temperature, is expressed as a percentage of the activity of a similar sample at zerotime. The data in Table II show that the recFSH formulation without the thioether compound methionine is less stable than the recFSH formulations with methionine, particularly following storage at temperatures above room temperature and for a prolonged time.

EXAMPLE 2

Formulations containing recombinant FSH-CTP.

Liquid formulations containing recombinant FSH-CTP, having the compositions as depicted in Table III, and denoted A-J, were prepared. 0.5 ml aliquots of each composition were stored, in a closed 2 ml vial, for 2 months at 8° C., 20° C., 30° C. and 40° C., respectively. In vitro bioactivity, determined as described in Example 1, are depicted in Table IV.

The data in Table IV show that the recFSH-CTP formulation without the thioether compound methionine is less stable than the recFSH-CTP formulations with methionine, particularly following storage at room temperature or above.

TABLE I

| | rec-FSH FORMULATIONS OF COMPOSITIONS A–J | | | | | | | | | |
|---|---|---|---|---|---|---|---|---|---|---|
| Compound# | A | B | C | D | E | F | G | H | I | J |
| recFSH | 50 IU | 50 IU | 50 IU | 50 IU | 50 IU | 600 IU | 600 IU | 600 IU | 600 IU | 600 IU |
| sucrose | 50 | 50 | 50 | 50 | 50 | 50 | 50 | 50 | 50 | 50 |
| sodium citrate dihydrate | 14.7 | 14.7 | 14.7 | 14.7 | 14.7 | 14.7 | 14.7 | 14.7 | 14.7 | 14.7 |
| polysorbate-20 | 0.2 | 0.2 | 0.2 | 0.2 | 0.2 | 0.2 | 0.2 | 0.2 | 0.2 | 0.2 |
| DL-methionine | — | 0.1 | 0.25 | 0.5 | 1.0 | — | 0.1 | 0.25 | 0.5 | 1.0 |
| pH | 7 | 7 | 7 | 7 | 7 | 7 | 7 | 7 | 7 | 7 |
| water to (ml) | 1.0 | 1.0 | 1.0 | 1.0 | 1.0 | 1.0 | 1.0 | 1.0 | 1.0 | 1.0 | in mg unless otherwise stated

B-E; G-J=this invention; A and F=reference

TABLE II

RETAINMENT OF IN-VITRO BIOACTIVITY of FSH COMPOSITIONS A-J IN TIME*

| | 1 month 8° C. | 1 month 30° C. | 1 month 40° C. | 2 months 8° C. | 2 months 30° C. | 2 months 40° C. |
|---|---|---|---|---|---|---|
| A | 90 | 83 | 63 | 95 | 84 | 52 |
| B | 86 | 82 | 68 | 95 | 87 | 60 |
| C | 76 | 72 | 67 | 83 | 89 | 69 |
| D | 92 | 98 | 85 | 95 | 92 | 73 |
| E | 97 | 83 | 73 | 100 | 83 | 72 |
| F | 87 | 84 | 71 | 90 | 80 | 55 |
| G | 97 | 98 | 84 | 87 | 85 | 67 |
| H | 89 | 90 | 78 | 96 | 99 | 83 |
| I | 99 | 85 | 75 | 96 | 88 | 73 |
| J | 92 | 90 | 82 | 100 | 89 | 75 |

*bioactivity is expressed as percentage of the activity at zerotime

TABLE III recFSH-CTP FORMULATIONS OF COMPOSITIONS A–J

| Compound# | A | B | C | D | E | F | G | H | I | J |
|---|---|---|---|---|---|---|---|---|---|---|
| recFSH-CTP | 5 μg | 5 μg | 5 μg | 5 μg | 5 μg | 30 μg | 30 μg | 30 μg | 30 μg | 30 μg |
| sucrose | 50 | 50 | 50 | 50 | 50 | 50 | 50 | 50 | 50 | 50 |
| sodium citrate dihydrate | 14.7 | 14.7 | 14.7 | 14.7 | 14.7 | 14.7 | 14.7 | 14.7 | 14.7 | 14.7 |
| polysorbate-20 | 0.2 | 0.2 | 0.2 | 0.2 | 0.2 | 0.2 | 0.2 | 0.2 | 0.2 | 0.2 |
| DL-methionine | — | 0.1 | 0.25 | 0.5 | 1.0 | — | 0.1 | 0.25 | 0.5 | 1.0 |
| pH | 7 | 7 | 7 | 7 | 7 | 7 | 7 | 7 | 7 | 7 |
| water to (ml) | 1.0 | 1.0 | 1.0 | 1.0 | 1.0 | 1.0 | 1.0 | 1.0 | 1.0 | 1.0 | in mg unless otherwise stated

B-E; G-J=this invention; A and F=reference

TABLE IV

RETAINMENT OF IN-VITRO BIOACTIVITY of recFSH-CTP COMPOSITIONS A-J IN TIME*

| | 2 months 8° C. | 2 months 20° C. | 2 months 30° C. | 2 months 40° C. |
|---|---|---|---|---|
| A | 89 | 87 | 75 | 50 |
| B | 87 | 90 | 89 | 74 |
| C | 93 | 95 | 88 | 66 |
| D | 89 | — | 83 | 60 |
| E | 103 | 101 | 97 | — |
| F | 78 | 75 | 68 | 43 |
| G | 84 | 90 | 89 | 70 |
| H | 88 | 85 | 85 | 74 |
| I | 92 | 92 | 90 | 74 |
| J | 88 | 92 | 89 | 72 |

*bioactivity is expressed as percentage of the activity at zerotime

We claim:

1. A stabilized liquid gonadotropin-containing formulation contained in a closed cartridge suited for storage, said formulation comprising a gonadotropin and stabilizing amounts of a polycarboxylic acid or salt thereof and of a thioether compound.

2. The liquid gonadotropin-containing formulation of claim 1, wherein the thioether compound is the amino acid methionine.

3. The liquid gonadotropin-containing formulation of claim 1 or 2, wherein the polycarboxylic acid is citric acid or the sodium salt thereof.

4. The liquid gonadotropin-containing formulation of claim 3, wherein the concentration of sodium citrate is 25–100 mM and the concentration of methionine is 1–10 mM.

5. The liquid gonadotropin-containing formulation of claim 1, further comprising a non-reducing sugar.

6. The liquid gonadotropin-containing formulation of claim 5, wherein the non-reducing sugar is sucrose in a concentration of 25–300 mM.

7. The liquid gonadotropin-containing formulation of claim 1, further comprising a non-ionic surfactant.

8. The liquid gonadotropin-containing formulation of claim 1, wherein the pH of the formulation is between 6.5 and 7.2.

9. The liquid gonadotropin-containing formulation of claim 1, wherein the gonadotropin is selected from luteinizing hormone (LH), human chorionic gonadotropin (hCG), follicle stimulating hormone (FSH), or derivatives thereof, and mixtures thereof.

10. The liquid gonadotropin-containing formulation of claim 9, wherein the gonadotropin is recombinant human FSH (recFSH) or recombinant FSH-CTP.

11. A method for preparing a stabilized liquid gonadotropin formulation comprising:

admixing, in an aqueous solution, at least one gonadotropin with a stabilizing amount of a polycarboxylic acid or a salt thereof, and a stabilizing amount of a thioether compound;

optionally dissolving an amount of a nonreducing disaccharide in the resulting admixture and optionally dissolving a nonionic surfactant in said admixture;

adjusting the pH of the resulting solution to a value between 6.5 and 7.2; and sealing the pH adjusted solution in a cartridge suited for storage.

12. A method for preparing a stabilized liquid gonadotropin formulation comprising:

admixing, in an aqueous solution, at least one gonadotropin with an amount of sodium citrate to a concentration of 25–100 mM, and an amount of methionine to a concentration of 1–10 mM;

optionally dissolving an amount of sucrose in the resulting admixture to a concentration of 25–300 mM and optionally dissolving a surfactant in said admixture;

adjusting the pH of the resulting solution to a value between 6.5 and 7.2; and sealing the pH adjusted solution in a cartridge suited for storage.

13. A method for treating infertility of a patient, comprising administering to the patient an effective amount of a formulation according to claim 1.

14. The liquid gonadotropin-containing formulation of claim 8, wherein the pH is 7.

* * * * *

UNITED STATES PATENT AND TRADEMARK OFFICE
CERTIFICATE OF CORRECTION

PATENT NO. : 5,929,028  
DATED : July 27, 1999  
INVENTOR(S) : Skrabanja et al.

Page 1 of 1

It is certified that error appears in the above-identified patent and that said Letters Patent is hereby corrected as shown below:

<u>Title page,</u>  
Item [22] replace "April 14, 1998" with -- January 14, 1998 --.

Signed and Sealed this

Fourteenth Day of May, 2002

*Attest:*

*Attesting Officer*

JAMES E. ROGAN  
*Director of the United States Patent and Trademark Office*